(12) United States Patent
Sanson et al.

(10) Patent No.: US 6,979,554 B1
(45) Date of Patent: Dec. 27, 2005

(54) CHEMICAL STRUCTURE HAVING AN AFFINITY FOR A PHOSPHOLIPID AND LABELING COMPOUND DIAGNOSE KIT AND DRUG COMPRISING THIS STRUCTURE

(75) Inventors: Alain Sanson, Gometz-le-Chatel (FR); Françoise Russo-Marie, Sèvres (FR); Jean-Michel Neumann, Gif sur Yvette (FR); Françoise Cordier-Ochsenbein, Paris (FR); Raphael Guerois, Heidelberg (DE)

(73) Assignees: Commissariat a l'Energie Atomique, Paris (FR); Universite Pierre et Marie Curie (Paris VI), Paris (FR)

( * ) Notice: Subject to any disclaimer, the term of this patent is extended or adjusted under 35 U.S.C. 154(b) by 0 days.

(21) Appl. No.: 09/787,923

(22) PCT Filed: Sep. 30, 1999

(86) PCT No.: PCT/FR99/02329

§ 371 (c)(1),
(2), (4) Date: Jun. 25, 2001

(87) PCT Pub. No.: WO00/20453

PCT Pub. Date: Apr. 13, 2000

(30) Foreign Application Priority Data

Oct. 2, 1998 (FR) .................................. 98 12366

(51) Int. Cl.[7] .................... A01N 37/18; A61K 38/00; C12P 21/06
(52) U.S. Cl. ..................... 435/69.1; 530/300; 514/2
(58) Field of Search .................. 435/69.1; 530/300, 530/350; 514/2, 12

(56) References Cited

U.S. PATENT DOCUMENTS 5,627,036 A 5/1997 Reutelingsperger

FOREIGN PATENT DOCUMENTS

WO   WO 91/09953   7/1991
WO   WO 92/19279   11/1992

OTHER PUBLICATIONS

Kaplan R, Jaye M, Burgess WH, Schlaepfer DD, Haigler HT. Cloning and expression of cDNA for human endonexin II, a Ca2+ and phospholipid binding protein.J Biol Chem. Jun. 15, 1988;263(17):8037-43.*

F. Cordier-Ochsenbein, et al., J. Mol. Biol., vol. 279, pp. 1163-1175, "Exploring the Folding Pathways of Annexin I, A Multidomain Protein. I, Non-Native Structures Stabilize the Partially Folded State of the Isolated Domain 2 of Annexin I", Jun. 1988.

K. Sano, et al., Biochemical and Biophysical Research Communications, vol. 144, No. 1, pp. 367-374, "Isolation and Sequence of A cDNA Clone For the Rat Pulmonary Surfactant-Associated Protein (PSP-A)", Apr. 14, 1987.

F. Macquaire, et al., Biochemistry, vol. 32, pp. 7244-7254, "Proton NMR Conformational Study of An Annexin I Fragment: Influence of A Phospholipidic Micellar Environment", 1993.

J. D. Ernst, et al., Biochemical and Biophysical Research Communications, vol. 200, No. 2, pp. 867-876, "Annexins Possess Functionally Distinguishable $Ca^{2+}$ and Phopholipid Binding Domains", Apr. 29, 1994.

R. Huber, et al., Febs Letters, vol. 275, No. 1,2, pp. 15-21, "The Calcium Binding Sites In Human Annexin V by Crystal Structure Analysis at 2.0 A Resolution", Nov. 1990.

W. Clark Still, Acc. Chem. Res., vol. 29, No. 3, pp. 155-163, "Discovery of Sequence-Selective Peptide Binding by Synthetic Receptors Using Encoded Combinatorial Libraries", 1996.

T. Schrader, J. Org. Chem., vol. 63, No. 2, pp. 264-272, "Toward Synthetic Adrenaline Receptors: Strong, Selective, and Biomimetic Recognition of Biologically Active Amino Alcohols by Bisphosphonate Receptor Molecules", 1998.

* cited by examiner

*Primary Examiner*—Jon Weber
*Assistant Examiner*—Sheridan Snedden
(74) *Attorney, Agent, or Firm*—Oblon, Spivak, McClelland, Maier & Neustadt, P.C.

(57) ABSTRACT

The present invention relates to a compound having affinity for a negatively charged phospholipid as well as to a detection molecule, to a conjugate and to a pharmaceutical composition comprising said compound.

Generally speaking, the compound of the present invention is useful for specific recognition of lipid vectors. It may be used in engineering and in the generation of compound for recognizing and sequestrating of negatively charged lipids, such as phosphatidyl-serine and phosphatidic acid.

The chemical structure of the present invention may have the construction (I).

27 Claims, 10 Drawing Sheets

Sequence ID No. 1

```
Met Ala Met Val Ser Glu Phe Leu Lys Gln Ala Trp Phe Ile
 1           5                   10
Glu Asn Glu Glu Gln Glu Tyr Val Gln Thr Val Lys Ser Ser
 15              20                  25
Lys Gly Gly Pro Gly Ser Ala Val Ser Pro Tyr Pro Thr Phe
     30              35              40
Asn Pro Ser Ser Asp Val Ala Ala Leu His Lys Ala Ile Met
         45              50                  55
Val Lys Gly Val Asp Glu Ala Thr Ile Ile Asp Ile Leu Thr
             60              65              70
Lys Arg Asn Asn Ala Gln Arg Gln Gln Ile Lys Ala Ala Tyr
                 75              80
Leu Gln Glu Thr Gly Lys Pro Leu Asp Glu Thr Leu Lys Lys
 85              90              95
Ala Leu Thr Gly His Leu Glu Glu Val Val Leu Ala Leu Leu
     100             105             110
```

Domain 2:
```
Lys Thr Pro Ala Gln Phe Asp Ala Asp Glu Leu Arg Ala Ala
         115             120             125
Met Lys Gly Leu Gly Thr Asp Glu Asp Thr Leu Ile Glu Ile
         130             135             140
Leu Ala Ser Arg Thr Asn Lys Glu Ile Arg Asp Ile Asn Arg
             145             150
Val Tyr Arg Glu Glu Leu Lys Arg Asp Leu Ala Lys Asp Ile
 155             160             165
Thr Ser Asp Thr Ser Gly Asp Phe Arg Asn Ala Leu Leu Ser
     170             175             180
Leu Ala Lys Gly Asp Arg Ser Glu Asp Phe Gly Val Asn Glu
         185             190             200
```

```
Asp Leu Ala Asp Ser Asp Ala Arg Ala Leu Tyr Glu Ala Gly
             205             210             215
Glu Arg Arg Lys Gly Thr Asp Val Asn Val Phe Asn Thr Ile
                 220             225
Leu Thr Thr Arg Ser Tyr Pro Gln Leu Arg Arg Val Phe Gln
 230             235             240
Lys Tyr Thr Lys Tyr Ser Lys His Asp Met Asn Lys Val Leu
     245             250             260
Asp Leu Glu Leu Lys Gly Asp Ile Glu Lys Cys Leu Thr Ala
         265             270             275
Ile Val Lys Cys Ala Thr Ser Lys Pro Ala Phe Phe Ala Glu
             280             285             290
Lys Leu His Gln Ala Met Lys Gly Val Gly Thr Arg His Lys
                 295             300
Ala Leu Ile Arg Ile Met Val Ser Arg Ser Glu Ile Asp Met
 305             310             315
Asn Asp Ile Lys Ala Phe Tyr Gln Lys Met Tyr Gly Ile Ser
     320             325             330
Leu Cys Gln Ala Ile Leu Asp Glu Thr Lys Gly Asp Tyr Glu
         335             340             345
Lys Ile Leu Val Ala Leu Cys Gly Gly Asn
             350             355
```

FIG. 6A: Human annexin I

Sequence ID No. 2

```
         Met Ala Gln Val Leu Arg Gly Thr Val Thr Asp Phe Pro Gly
         1               5                   10
         Phe Asp Glu Arg Ala Asp Ala Glu Thr Leu Arg Lys Ala Met
         15                  20                  25
         Lys Gly Leu Gly Thr Asp Glu Glu Ser Ile Leu Thr Leu Leu
         30                  35                  40
Domain 1 Thr Ser Arg Ser Asn Ala Gln Arg Gln Glu Ile Ser Ala Ala
         45                  50                  55
         Phe Lys Thr Leu Phe Gly Arg Asp Leu Leu Asp Asp Leu Lys
                 60                  65                  70
         Ser Glu Leu Thr Gly Lys Phe Glu Lys Leu Ile Val Ala Leu
                     75                  80
         Met Lys Pro Ser Arg Leu Tyr Asp Ala Tyr Glu Leu Lys His
         85                  90                  95
         Ala Leu Lys Gly Ala Gly Thr Asn Glu Lys Val Leu Thr Glu
             100                 105                 110
         Ile Ile Ala Ser Arg Thr Pro Glu Glu Leu Arg Ala Ile Lys
             115                 120                 125
         Gln Val Tyr Glu Glu Glu Tyr Gly Ser Ser Leu Glu Asp Asp
                     130                 135                 140
         Val Val Gly Asp Thr Ser Gly Tyr Tyr Gln Arg Met Leu Val
                         145                 150
         Val Leu Leu Gln Ala Asn Arg Asp Pro Asp Ala Gly Ile Asp
         155                 160                 165
         Glu Ala Gln Val Glu Gln Asp Ala Gln Ala Leu Phe Gln Ala
             170                 175                 180
         Gly Glu Leu Lys Trp Gly Thr Asp Glu Glu Lys Phe Ile Thr
                 185                 190                 195
         Ile Phe Gly Thr Arg Ser Val Ser His Leu Arg Lys Val Phe
                     200                 205                 210
         Asp Lys Tyr Met Thr Ile Ser Gly Phe Gln Ile Glu Glu Thr
                         215                 220
         Ile Asp Arg Glu Thr Ser Gly Asn Leu Glu Gln Leu Leu Leu
         225                 230                 235
         Ala Val Val Lys Ser Ile Arg Ser Ile Pro Ala Tyr Leu Ala
             240                 245                 250
         Glu Thr Leu Tyr Tyr Ala Met Lys Gly Ala Gly Thr Asp Asp
                 255                 260                 265
         His Thr Leu Ile Arg Val Met Val Ser Arg Ser Glu Ile Asp
                     270                 275                 280
         Leu Phe Asn Ile Arg Lys Glu Phe Arg Lys Asn Phe Ala Thr
                         285                 290
         Ser Leu Tyr Ser Met Ile Lys Gly Asp Thr Ser Gly Asp Tyr
         295                 300                 305
         Lys Lys Ala Leu Leu Leu Leu Cys Gly Glu Asp Asp
             310                 315                 320
```

FIG. 6B Human annexin V

Sequence ID No. 3

```
        Met  Ala  Ser  Ile  Trp  Val  Gly  His  Arg  Gly  Thr  Val  Arg  Asp
        1              5                        10
        Tyr  Pro  Asp  Phe  Ser  Pro  Ser  Val  Asp  Ala  Glu  Ala  Ile  Gln
        15                  20                       25
        Lys  Ala  Ile  Arg  Gly  Ile  Gly  Thr  Asp  Glu  Lys  Met  Leu  Ile
                  30                      35                      40
        Ser  Ile  Leu  Thr  Glu  Arg  Ser  Asn  Ala  Gln  Arg  Gln  Leu  Ile
                       45                      50                           55
        Val  Lys  Glu  Tyr  Gln  Ala  Ala  Tyr  Gly  Lys  Glu  Leu  Lys  Asp
                            60                      65                       70
        Asp  Leu  Lys  Gly  Asp  Leu  Ser  Gly  His  Phe  Glu  His  Leu  Met
                            75                      80
       ┌Val  Ala  Leu  Val  Thr  Pro  Pro  Ala  Val  Phe  Asp  Ala  Lys  Gln
       │85                      90                      95
       │Leu  Lys  Lys  Ser  Met  Lys  Gly  Ala  Gly  Thr  Asn  Glu  Asp  Ala
       │          100                 105                 110
Domain 2│Leu  Ile  Glu  Ile  Leu  Thr  Thr  Arg  Thr  Ser  Arg  Gln  Met  Lys
       │               115                 120                      125
       │Asp  Ile  Ser  Gln  Ala  Tyr  Tyr  Thr  Val  Tyr  Lys  Lys  Ser  Leu
       │                    130                      135                     140
       │Gly  Asp  Asp  Ile  Ser  Ser  Glu  Thr  Ser  Gly  Asp  Phe  Arg  Lys
       │                         145                     150
       └Ala  Leu  Leu  Thr  Leu  Ala  Asp  Gly  Arg  Arg  Asp  Glu  Ser  Leu
        ─155                      160                     165
        Lys  Val  Asp  Glu  His  Leu  Ala  Lys  Gln  Asp  Ala  Gln  Ile  Leu
             170                      175                     180
        Tyr  Lys  Ala  Gly  Glu  Asn  Arg  Trp  Gly  Thr  Asp  Glu  Asp  Lys
                  185                      190                     195
        Phe  Thr  Glu  Ile  Leu  Cys  Leu  Arg  Ser  Phe  Pro  Gln  Leu  Lys
                       200                     205                          210
        Leu  Thr  Phe  Asp  Glu  Tyr  Arg  Asn  Ile  Ser  Gln  Lys  Asp  Ile
                            215                     220
        Val  Asp  Ser  Ile  Lys  Gly  Glu  Leu  Ser  Gly  His  Phe  Glu  Asp
        225                      230                     235
        Leu  Leu  Leu  Ala  Ile  Val  Asn  Cys  Val  Arg  Asn  Thr  Pro  Ala
             240                      245                     250
        Phe  Leu  Ala  Glu  Arg  Leu  His  Arg  Ala  Leu  Lys  Gly  Ile  Gly
                  255                      260                     270
        Thr  Asp  Glu  Phe  Thr  Leu  Asn  Arg  Ile  Met  Val  Ser  Arg  Ser
                       275                          280                     285
        Glu  Ile  Asp  Leu  Leu  Asp  Ile  Arg  Thr  Glu  Phe  Lys  Lys  His
                            290                     295
        Tyr  Gly  Tyr  Ser  Leu  Tyr  Ser  Ala  Ile  Lys  Ser  Asp  Thr  Ser
        300                      305                     310
        Gly  Asp  Tyr  Glu  Ile  Thr  Leu  Leu  Lys  Ile  Cys  Gly  Gly  Asp  Asp
        315                      320                     325
```

FIG. 6C : Human annexin III

Sequence ID No. 4

Domain 1:
```
Met Ala Thr Lys Gly Gly Thr Val Lys Ala Ala Ser Gly Phe
 1           5                  10
Asn Ala Met Glu Asp Ala Gln Thr Leu Arg Lys Ala Met Lys
15              20                  25
Gly Leu Gly Thr Asp Glu Asp Ala Ile Ile Ser Val Leu Ala
        30              35                  40
Tyr Arg Asn Thr Ala Gln Arg Gln Glu Ile Arg Thr Ala Tyr
         45                  50                  55
Lys Ser Thr Ile Gly Arg Asp Leu Ile Asp Asp Leu Lys Ser
                60                  65                  70
Glu Leu Ser Gly Asn Phe Glu Gln Val Ile Val Gly Met Met
                    75                  80
Thr
85
```

Séquence ID n°5

Domain 2:
```
Pro Thr Val Leu Tyr Asp Val Gln Glu Leu Gln Arg Lys Gly
86               90                  95
Ala Met Lys Gly Ala Gly Thr Asp Glu Gly Cys Leu Ile Glu
        100             105                 110
Ile Leu Ala Ser Arg Thr Pro Glu Glu Ile Arg Arg Ile Asn
            115                 120                 125
Gln Thr Tyr Gln Leu Gln Tyr Gly Arg Ser Leu Glu Asp Asp
                130                 135                 140
Ile Arg Ser Asp Thr Ser Phe Met Phe Gln Arg Val Leu Val
                145                 150
```
```
Ser Leu Ser Ala Gly Gly Arg Asp Glu Gly Asn Tyr Leu Asp
155             160                 170
Asp Ala Leu Val Arg Gln Asp Ala Gln Asp Leu Tyr Glu Ala
    175                 180                 185
Gly Glu Lys Lys Trp Gly Thr Asp Glu Val Lys Phe Leu Thr
        190                 195                 200
Val Leu Cys Ser Arg Asn Arg Asn His Leu Leu His Val Phe
            205                 210                 215
Asp Glu Tyr Lys Arg Ile Ser Gln Lys Asp Ile Glu Gln Ser
                220                 225
Ile Lys Ser Glu Thr Ser Gly Ser Phe Glu Asp Ala Leu Leu
230                 235                 240
Ala Ile Val Lys Cys Met Arg Asn Lys Ser Ala Tyr Phe Ala
    245                 250                 255
Glu Lys Leu Tyr Lys Ser Met Lys Gly Leu Gly Thr Asp Asp
        260                 265                 270
Asn Thr Leu Ile Arg Val Met Val Ser Arg Ala Glu Ile Asp
            275                 280                 285
Met Leu Asp Ile Arg Ala His Phe Lys Arg Leu Tyr Gly Lys
                290                 295
Ser Leu Tyr Ser Phe Ile Lys Gly Asp Thr Ser Gly Asp Tyr
300                 305                 310
Arg Lys Val Leu Leu Val Leu Cys Gly Gly Asp Asp
    315                 320             325
```

FIG. 6D: Human annexin IV

Compound (I) + phosphatidylserine

CHEMICAL STRUCTURE HAVING AN AFFINITY FOR A PHOSPHOLIPID AND LABELING COMPOUND DIAGNOSE KIT AND DRUG COMPRISING THIS STRUCTURE

CROSS-REFERENCE TO RELATED APPLICATIONS

The present application is National Stage (371) of International application PCT/FR99/02329, filed on Sep. 30, 1999, which claims priority to French Application No. FR 98/12366, filed on Oct. 2, 1998.

TECHNICAL FIELD

The present invention relates to a chemical structure having an affinity for a phospholipid as well as to a detection molecule, to a conjugate and to a pharmaceutical composition comprising said structure.

Generally speaking, the chemical structure of the present invention is useful for specific recognition of lipid vectors. It may be used for engineering and generation of compounds for recognizing and sequestrating lipids, notably negatively charged lipids, such as phosphatidylserine and/or phosphatidic acid.

These lipids play an important role notably in cellular signaling and they may be present at the external surface of cell membranes and/or circulate in the blood medium following very diverse pathological events.

Diverse cellular events result in the occurrence of phosphatidylserine (PS) at the external cell surface, whereby these events may result either from an accidental or pathological alteration of the cell, or from a programmed cellular event such as cell death or apoptosis. Occurrence of PS at the external surface of cells therefore forms an important "primary message" revealing the existence of a malfunction. In the case of a blood coagulation process, the mechanism is well described: the alteration of the endothelial cells of the blood vessels, either for accidental reasons or for more complex pathological reasons, causes the occurrence of this PS message at the external surface of cells in contact with the blood medium. This message is immediately recognized by certain circulating proteins which then trigger a cascade of events resulting in the well-known blood coagulation phenomenon.

The invention makes the most of the property of the structure which it provides of binding itself, whether in presence of calcium or not, to lipids and notably to negatively charged ones, for developing useable compounds as research, diagnose and therapeutic tools in the field of recognition of lipid effectors as a rule and of detection of apoptosis, blood coagulation disorders, of septic chock and in particular acute inflammatory pathologies.

As regards research and diagnose, the structure of the invention may for example be coupled with detection molecules, for example a fluorescent molecule, the avidin-biotin complex, a short-lived radioelement or a paramagnetic compound. For instance, with these detection molecules, it is possible to detect apoptotic cells or to recognize negatively charged membrane microdomains.

The structure of the present invention may therefore be used for "in vitro" detection of pathologies involving occurrence of negative charges at the surface of the cells and release of microvesicles into the blood.

The structure of the present invention may also be used when it is coupled for example with a short lived radioelement, for "in vitro" detection of thrombotic areas upon vascular, in particular cerebro-vascular accidents of any kind, by using imaging systems. This structure may further be used when it is coupled with a paramagnetic compound such as a gadolinium complex for "in vivo" detection of thrombotic, in particular brain areas, by using magnetic resonance imaging (MRI).

As for therapeutics, generally speaking, the structure of the present invention may be used by itself or coupled with a therapeutic molecule in order to prepare a drug which may for example be used orally. For example, such a drug may be used for targeting this molecule towards areas having negative charges such as tumors having centers of apoptotic cells or inflammatory tumors.

The structure of the present invention may for example be coupled with thrombolytic action molecules in order to prepare a drug which may be for example used orally as an anticoagulant in the treatment and prophylaxis of thrombosis or to prepare a molecule covering all thrombogenic biomaterials. The structure of the present invention may therefore be used for targeting thrombolytic molecules at the site of the thrombus or towards the thrombogenic areas.

In another exemplary application of the present invention, the structure of the invention may be used by itself or coupled with an anti-inflammatory molecule in order to prepare a drug which may be used orally, for example in acute pathologies like asthma, haemorrhagic rectocolitis (HRC), Crohn's disease, septic shock, collagenosis and arthritis.

State of the Art

A family of proteins, called annexins, have been described in the prior art as having reversible functional anchoring to the cell membrane, controlled by the calcium concentration and the presence of anionic phospholipids. Annexins form a protein family expressed in very diverse tissues, both in animals and in plants. It seems that they are neither expressed in bacteria nor in yeasts.

The structure of annexins includes four domains of about 70 amino acids or residues, very fairly homologous in sequence but of a nearly identical topology.

Appended FIG. 1A is a diagram of the general topology of an annexin and appended FIG. 1B is a diagram of the topology of a domain of annexin bearing a calcium site. In FIG. 1A, C represents the C-terminal end of this protein, N represents the N-terminal end of this protein. Domains, noted as D1–D4, are associated in two modules, a covalent one D2D3, and the other, a non-covalent one D1D4. In FIG. 1B, A represents a first α helix, B represents a third α helix, D represents a fourth α helix, E represents a fifth α helix and Ca represents the calcium atom. Association of these helices forms the consensus structure for an annexin domain.

Presently, their biological roles still remain undefined.

In document WO 92/19279, J. Tait describes conjugates having an affinity for phospholipids. In particular, he describes the use of annexin, in particular annexin V, for producing an active conjugate usable as a thrombolytic agent.

Unfortunately, the described conjugate in this document is prepared from entire annexin by a genetic recombination method. Consequently, a great number of drawbacks occur, notably a low yield, a high production cost and a fragile conjugate is obtained because of its complex protein portion.

DESCRIPTION OF THE INVENTION

Specifically, the object of the present invention is to provide a chemical structure having a specific affinity with a phospholipid. The chemical structure of the invention notably has the advantage of being chemically stable and able to be produced in a reproducible way, with a high yield and very reduced production costs as compared with prior art compounds.

The structure of the present invention is characterized in that it comprises at least a chemical platform U, V, W, X, Y including six residues RL1, RL2, RL3, RL4, RL5, RL6 supporting a set of chemical functions which may bind to said phospholipid, called, L1, L2, L3, L4, L5, L6 respectively, whereby these chemical functions define at least partly the affinity of said structure for said phospholipid, said structure having one of the following constructions (I), (II) and (III):

DESSINSx3 wherein U, $U^1$, $U^2$, V, W, $W^1$, $W^2$, X, Y, Z are independently a natural or non-natural amino-acid, a peptide consisting of natural or non-natural amino-acids, a carbon chain, or carbon cyclic group(s), wherein RL1 to RL6 are selected from the molecules having the binding chemical functions L1 to L6, respectively, wherein said chemical functions comprise either at least a positively charged donor of a hydrogen bond, or at least a negatively charged acceptor of a hydrogen bond, and wherein U, $U^1$, $U^2$, V, W, $W^1$, $W^2$, X, Y, Z are such that RL6 and RL1 are distant from 0.65 to 0.95 nm, L6 and L1 are distant from 0.65 to 0.9 nm, RL1 and RL2 are distant from 0.45 to 0.65 nm, L1 and L2 are distant from 0.4 to 0.55 nm, RL2 and RL3 are distant from 0.5 to 1.05 nm, L2 and L3 are distant from 0.4 to 0.6 nm, RL3 and RL4 are distant from 0.5 to 0.8 nm, L3 and L4 are distant from 0.35 to 0.5 nm, RL4 and RL5 are distant from 0.45 to 0.75 nm, and L4 and L5 are distant from 0.4 to 0.55 nm, RL5 and RL6 are distant from 0.4 to 1.2 nm, L5 and L6 are distant from 0.4 to 0.6 nm.

According to the invention, in the structure of constructions (I), (II) or (III), L1, L2, L3 and L6 may each have at least a positively charged donor of a hydrogen bond, and L4 and L5 may each have at least one negatively charged acceptor of a hydrogen bond.

According to the invention, in the structure of construction (I), (II), or (III), U, V, W, X, Y and Z may be peptides consisting of natural or non-natural amino-acids, and RL1 to RL6 are amino acids selected from a set comprising Lys, Arg, Orn, Ser, Thr, Asp and Glu, or analogs of the latter, L1 to L6 are the charge-bearing functions of the side chains of said amino acids.

According to the invention, in the structure of construction (I), (II) or (III), RL1 to RL6 may be positioned in the space formed by U, V, W, X, Y, Z so that the chemical binding functions L1 to L6 are directly accessible to the phospholipid, from their side chains respectively.

According to the invention, the structures of construction (I), (II) or (III) may further comprise a calcium site where the calcium ion complexed by this site forms one of the ligands of the phospholipid.

The present invention also provides a chemical structure which is characterized in that it comprises at least a chemical platform a, a', b, b', c, d, e, f, g, h, i, j, k, l including 11 residues, LR1, LR2, LR3, LR4, LR5, RL6, RCa1, RCa2, RCa3, RCa4 and RCa5 supporting a set of chemical functions which may bind to said phospholipid, called L1, L2, L3, L4, L5, L6 respectively and a set of chemical functions for binding a calcium atom called LCa1, LCa2, LCa3, LCa4, LCa5 respectively, wherein these chemical functions RL1 to RCa5 define at least partly the affinity of said structure for said phospholipid, said structure having one of the following constructions (IV), (V) and (VI):

DESSINSx3 wherein a, a', b, b', c, d, e, f, g, h, i, j, k, l, are independently a natural or non-natural amino acid, a peptide consisting of natural or non-natural amino acids, a carbon chain, or carbon cyclic group(s), wherein LR1 to LR6 and RCa1 to RCa5 are selected from molecules having chemical binding functions L1 to L6 and LCa1 to LCa5 respectively, wherein said chemical functions L1 to L6 comprise either at least a positively charged donor of a hydrogen bond, or at least a negatively charged acceptor of a hydrogen bond, said chemical functions LCa1 to LCa5 comprising an oxygen atom, and wherein a in the structures of construction (IV) and (V) is such that RL6 and RCa5 are distant from 0 to 0.35 nm and such that L6 and LCa5 are distant from 0 to 0.3 nm, b in the structures of construction (IV) and (V) is such that RCa5 and RCa4 are distant from 0 to 0.35 nm and such that LCa5 and LCa4 are distant from 0.2 to 0.3 nm, b' in the structure of construction (VI) is such that RL6 and RCa4 are distant from 0 to 0.35 nm and such that L6 and LCa4 are distant from 0 to 0.35 nm, c and d are such that RCa4 and RCa3 are distant from 0.5 to 0.9 nm, LCa4 and LCa3 are distant from 0.2 to 0.4 nm, RCa3 and RCa2 are distant from 0.35 to 0.6 nm, and LCa3 and LCa2 are distant from 0.22 to 0.3 nm, e, f, g, in the structures of construction (IV), (V), (VI) are such that RL1 and RL2 are distant from 0.45 to 0.65 nm, RCa1 to RCa2 are distant from 0.4 to 0.55 nm, L1 and L2 are distant from 0.4 to 0.55 nm and LCa1 and LCa2 are distant from 0.3 to 0.4 nm, h, i, j and k are such that RL2 and RL3 are distant from 0.5 to 1.05 nm, L2 and L3 are distant from 0.4 to 0.6 nm, RL3 and RL4 are distant from 0.5 to 0.8 nm, L3 and L4 are distant from 0.35 to 0.5 nm, RL4 and RL5 are distant from 0.45 to 0.75 nm, L4 and L5 are distant from 0.4 to 0.55 nm, RL5 and RL6 are distant from 0.4 to 1.2 nm, and L5 and L6 are distant from 0.4 to 0.6 nm, a' in the structure of construction (VI) is such that RL5 and RL6 are distant from 0.4 to 1.2 nm and such that L5 and L6 are distant from 0.4 to 0.6 nm, and b' in the structure of construction (VI) is such that RL6 and RCa4 are distant from 0 to 0.35 nm and such that L6 and LCa4 are distant from 0 to 0.35 nm, whereby the structure may be either closed or open at a and/or h.

When the preceding distances a, b, b' are indicated as being possibly zero, it is understood that the two sets (RL6-L6 and RCa5-LCa5) and/or both sets (RCa4-LCa4 and RCa5-LCa5) and or both sets (RL6-L6 and RCa4-LCa4) separately form a single and same set.

The platforms according to the invention consist of a set of structural chemical groups which may comprise a sufficient number of cyclic groups in order to provide stiffness compatible with the affinity towards the phospholipid.

The measured distances when RLs and RCas are amino acids, may be measured between the α carbon atoms of these amino acids in the aforementioned structures (I) to (VI).

These structures may be synthesized by conventional synthesis methods of organic chemistry and of protein chemistry, by genetic recombination, by genetic engineering, etc.

Examples of such structures are notably given in "Discovery of Sequence-Selective Peptide Binding by Synthetic Receptors Using Encoded Combinatorial Libraries", W. C. Still, Acc. Chem. Res., 1996, 29, 155–163 and in "Toward Synthetic Adrenaline Receptors: Strong, Selective and Biomimetic Recognition of Biologically Active Amino Alcohols by Bisphosphonate Receptors Molecules", T. Shrader, J. Org. Chem., 1998, 63, 264–272.

According to the invention, in the structure of construction (IV), (V) or (VI), L1, L2, L3 and L6 may each have at least a positively charged donor of a hydrogen bond, and L4, L5, LCa5, LCa4, LCa3, LCa2 and LCa1 may each have at least a negatively charged acceptor of a hydrogen bond.

According to the invention, in the structure of construction (I), (II), (III), RL1, RL2, RL3 and RL6 may be independently selected from Arg, Lys, Orn; RL4 may be independently selected from Asp or Glu; and RL5 may be independently selected from Ser, Thr, Asp or Glu, whereby the side chains of these amino acids have chemical functions for binding to the phospholipids L1 to L6, respectively.

According to the invention, in the structure of construction (IV), (V) or (VI), a or a', b or b', c, d, e, f, g, h, i, j, k may be peptides consisting of natural or non-natural amino acids, and RL1 to RL5 may be amino acids selected from a set comprising Lys, Arg, Orn, Ser, Thr, Asp and Glu, or analogs thereof, RL6 may be Asp or Glu or analogs of the latter, L1 to L6 and LCa1 to LCa5 may be the charge-bearing functions of the side chains of said amino acids, and RCa1 to RCa5 may be natural or non-natural amino acids.

According to the invention, in the structure of constructions (IV), (V) or (VI), the carbon atoms RL1 to RL6 and RCa1 to RCa2 may be positioned in the space formed by a, b, c, d, e, f g, h, i, j and k so that the chemical binding functions L1 to L6 respectively and the positive charges of the calcium atom when the latter is bound to the bond functions LCa1 to LCa5, are directly accessible to the phospholipid.

According to the invention, in the structure of construction (I), (II), (II), (IV), (V) or (VI), at least a portion of the platform may be a portion of a domain of the annexin or of a modified domain of the annexin, comprising at least one of said residual ligands RL1 to RL6, having said functions L1 to L6 respectively for binding to the phospholipid.

According to the invention, in the structure of construction (I), (II), (III), (IV), (V), or (VI), the platform may be a portion of a domain of the annexin or a modified annexin domain, wherein said portion of the annexin domain comprises said residual ligands RL1 to RL6 having said functions L1 to L6, respectively.

According to the invention, the annexin domain is selected from the domain 1 of annexin V shown in FIG. 6b, domain 2 of annexin I shown in FIG. 6a, domain 2 of annexin III shown in FIG. 6c and domain 1 and 2 of annexin IV shown in FIG. 6d.

According to the invention, the residual ligands RL1 to RL6 respectively may be either the residues Arg25, Lys29, Arg63, Asp68, Ser71 and Glu72 of domain 1 of annexin V shown in FIG. 6b or residues Arg124, Lys128, Arg162, Asp167, Ser170 and Asp171 of domain 2 of annexin I shown in FIG. 6a, or residues Lys100, Lys104, Lys138, Asp143, Ser146 and Glu147 of domain 2 of annexin III shown in FIG. 6c, or residues Arg97, Lys101, Arg135, Asp140, Ser143 and Asp144 of domain 2 of annexin IV shown in FIG. 6d, or residues Arg24, Lys28, Arg62, Asp67, Ser70 and Glu71 of domain 1 of annexin IV shown in FIG. 6d.

The present invention also provides a chemical structure with an affinity for a phospholipid, characterized in that it comprises a molecule of the following formula (VII):

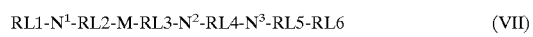

RL1-N$^1$-RL2-M-RL3-N$^2$-RL4-N$^3$-RL5-RL6    (VII)

wherein N$^1$ to N$^3$ each independently represent 1 to 4 independently selected, natural or non-natural, amino acids and wherein M is a peptide consisting of 1 to 100 natural or non-natural amino acids;

wherein RL 1, RL2, and RL3 are independently selected from Lys, Arg or Orn; RL4 and RL6 are independently selected from Asp or Glu; and RL5 is independently selected from Ser, Thr, Asp, or Glu, wherein said structure is linear or cyclic.

According to the invention, N$^1$ may represent three amino acids, N$^2$ may represent four amino acids, and N$^3$ may represent two amino acids in the structure of formula VII.

In the structure according to the invention, M may be for example a peptide consisting of 33 natural or non-natural amino acids.

According to the invention, the structure of formula (VII) may be a peptide sequence selected from the peptide sequence from Arg 124 to Asp 171 in the ID No.1 sequence shown in FIG. 6a, the peptide sequence from Arg25 to Glu72 in the ID No.2 sequence shown in FIG. 6b, the peptide sequence from Lys100 to Glu147 in the ID No.3 sequence shown in FIG. 6c, the sequence from Arg24 to Glu71 in the ID No.4 sequence shown in FIG. 6d, the sequence from Arg97 to Asp144 in ID No.5 sequence shown in FIG. 6d, or a modified sequence of these sequences provided that RL 1, RL2, and RL3 are independently selected from Lys, Arg, or Orn;

RL4 and RL6 independently selected from Asp or Glu, and RL5 is independently selected from Ser, Thr, Asp or Glu.

The present invention also provides a chemical structure with an affinity for a phospholipid, comprising at least a portion of a peptide sequence selected from ID No.1 sequence shown in FIG. 6a, ID No.2 sequence shown in FIG. 6b, ID No.3 sequence shown in FIG. 6c, and ID No.4 and No.5 sequences shown in FIG. 6d or a modified sequence of the latter.

The present invention also provides a chemical structure with an affinity for a negatively charged phospholipid, comprising a cyclic peptide sequence of the following formula (VIII):

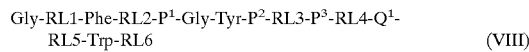

Gly-RL1-Phe-RL2-P$^1$-Gly-Tyr-P$^2$-RL3-P$^3$-RL4-Q$^1$-RL5-Trp-RL6    (VIII)

wherein RL1 are independently selected from Lys, Orn and Arg; RL2 and RL3 are Arg; RL4, RL5, and RL6 are independently selected from Asp and Glu;

wherein P$^1$, P$^2$ and P$^3$ are independently selected from Ser and Thr; wherein Q$^1$ is selected from Gly and Met.

The aforementioned chemical structures may further comprise a calcium site where the calcium ion complexed by this site forms one of the ligands of the negatively charged phospholipid. The calcium site may be for example a calcium site analogous to the one of the annexins or phospholipids A2. These calcium sites are known to one skilled in the art.

According to the invention, all the aforementioned chemical structures may have an affinity for a phospholipid selected from a phosphatidylserine, a phosphatidylethanolamine, a phosphatidylinositol, a phosphatidic acid, and a cardiolipin, the lipid chain(s) of the phospholipids may for example comprise from 4 to 23 carbon atoms. For example, the phospholipid may have a arachidonic acid chain, for example for phosphatidylserine.

The present invention also provides a chemical assembly with an affinity for a phospholipid, comprising at least two of the chemical structures of the present invention, identical or different, wherein said structures are bound.

For example, in a chemical assembly of the present invention, at least one of the chemical structures may be one of the peptide chemical structures described earlier.

The assemblies according to the invention may therefore be composed for example of identical of different structures. For example, the assembly may be an appropriate covalent assembly of two structures according to the invention, for example domains 1 and 4 according to the invention, of a same annexin. This assembly may for example, include a domain 4 according to the invention, modified by genetic engineering for the purpose of introducing a calcium and phospholipid site identical to the one of domain 1 of the invention.

These domains may for example stem from annexins I and V.

These assemblies may notably have the purpose of increasing the affinity of structures of the present invention, for the phospholipid, for example for a negatively charged phospholipid. For example they may be made by inserting a flexible peptide bond, for example polyglycine, between the chemical structures of the invention.

The structures and assemblies of the present invention exhibit an affinity for phospholipids, and notably for those that are negatively charged, better than 0.1 $\mu$M. They may comprise a portion of an annexin or one of its derivatives. This annexin may be a natural annexin or a modified one by conventional chemistry or genetic engineering means.

The present invention also provides a method for producing a chemical structure comprising the steps consisting of preparing a cDNA comprising a coding sequence of bases for said chemical structure, inserting the cDNA in an appropriate expression vector, transforming an appropriate host cell for replicating the plasmid and producing said structure by translation of said cDNA.

According to the invention, in this method, the vector may be a plasmid, for example vector pGEX-2T.

In the method according to the invention, the appropriate host cell may be E. Coli for example.

For example, for producing the structure according to the invention, it is possible to start with domain 1 of the annexin I and then modify the sequence in such a way that the RL residues defined earlier and possibly the RCa residues occur in the sequence. Thus, through conventional genetic engineering methods, a coding cDNA for the modified sequence may be produced and the structure of the present invention may be obtained very easily. The structure according to the invention, when it exhibits at least a peptide portion, may also be produced by a conventional solid phase chemical synthesis method.

An example of the modification of the sequence of domain 1 of the invention of annexin I may consist in replacing His52 with Arg, Met56 with Lys or Arg, Val57 with Gly, Val60 with Thr, possibly Lys90 with Arg, Thr95 with Asp, Lys98 with Ser or Thr, and Ala99 with Asp or Glu. These modifications may also be made on other domains.

These modifications may notably have the role of increasing the general stability of the structure or of the domain as regards temperature, pH, and ionic conditions of the medium used; reducing its possible general toxicity properties towards human organism; increasing its affinity for negatively charged phospholipids; and increasing its general affinity for cell membranes.

According to the invention, the modification of a domain may also have the role of developing the affinity of the structure for a, e.g. negatively charged, phospholipid, and even of restoring an affinity at least equal to that possessed by so-called wild annexin, in the absence of calcium.

The modification may for example target the residue, the so-called Asp or Glu bidentate residue of calcium (RL6) of the domain(s) bearing a phosphatidylserine site, in order to replace them with one of the Lys or Orn residues.

Another modification, for example of domain 1 of annexin V, may consist in replacing Glu72 with Lys or Orn, and/or Thr33 with Lys or Orn.

According to the invention, the chemical structure or assembly of the present invention may be used for preparing a drug.

For example, the drug may be selected from a drug for treating a thrombosis, a drug for treating a tumor, a drug with an anti-inflammatory action.

According to the invention, the chemical structure or assembly according to the invention may be coupled with a labelling molecule for forming a labelling compound.

According to the invention, the labelling molecule may be selected for example from a fluorescent molecule, the avidin-biotin complex, a radioelement and a paramagnetic compound.

The present invention also provides a diagnose kit comprising an aforementioned structure or assembly.

This diagnose kit may for example further comprise an adequate reagent for detecting said labelling molecule.

The present invention also provides an analysis and detection kit for negative charges at the surface of cells, characterized in that it comprises a chemical structure or assembly of the present invention.

The present invention also provides an analysis and detection kit for microvesicles in blood, characterized in that it comprises a chemical structure or assembly of the present invention coupled with a tracer.

Other advantages and features of the present invention will further become apparent upon reading the illustrative and non-limiting examples which follow, with reference to the appended figures.

BRIEF DESCRIPTION OF THE FIGURES

FIG. 6a represents the sequence of annexin I, noted as ID No.1 sequence, wherein the sequence of domain 2 of the present invention has been underlined;

FIG. 6*b* represents the sequence of annexin V, noted as ID No.2 sequence, wherein the sequence of domain 1 of the present invention has been underlined;

FIG. 6*c* represents the sequence of annexin III, noted as ID No.3 sequence wherein the sequence of domain 2 of the present invention has been underlined;

FIG. 6*d* represents the sequence of annexin IV noted as ID No.4 sequence and ID No.5 sequence wherein the sequences of domains 1 and 2 of the present invention have been underlined;

EXAMPLES

Example 1

Expression and Purification of Peptides with ID No.1 and ID No.2 Sequences of the Present Invention ID No.1 and ID No.2 sequences of annexins I and V were prepared by overexpression in *E. Coli* according to the same protocol as the one described by F. Cordier-Ochsenbein et al. in J. Mol. Biol. 279, 1177–1185.

Figure 1B:
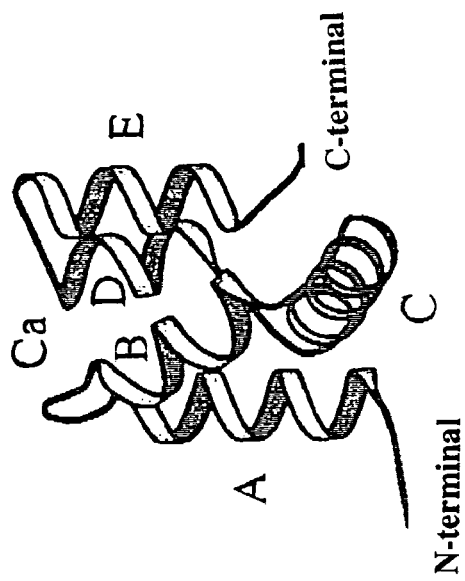
FIG. 1B is a schematic representation of the structure of a domain of an annexin including a calcium site.
Figure 1A:
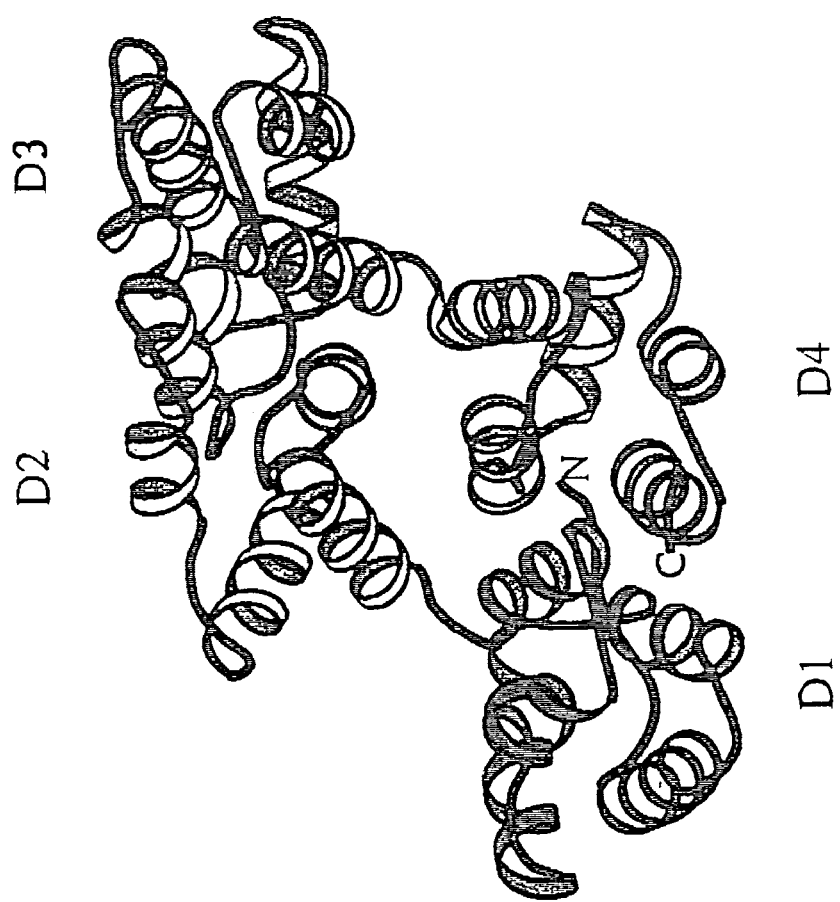
FIG. 1A is a schematic representation of the general structure of annexins.
Figure 2:
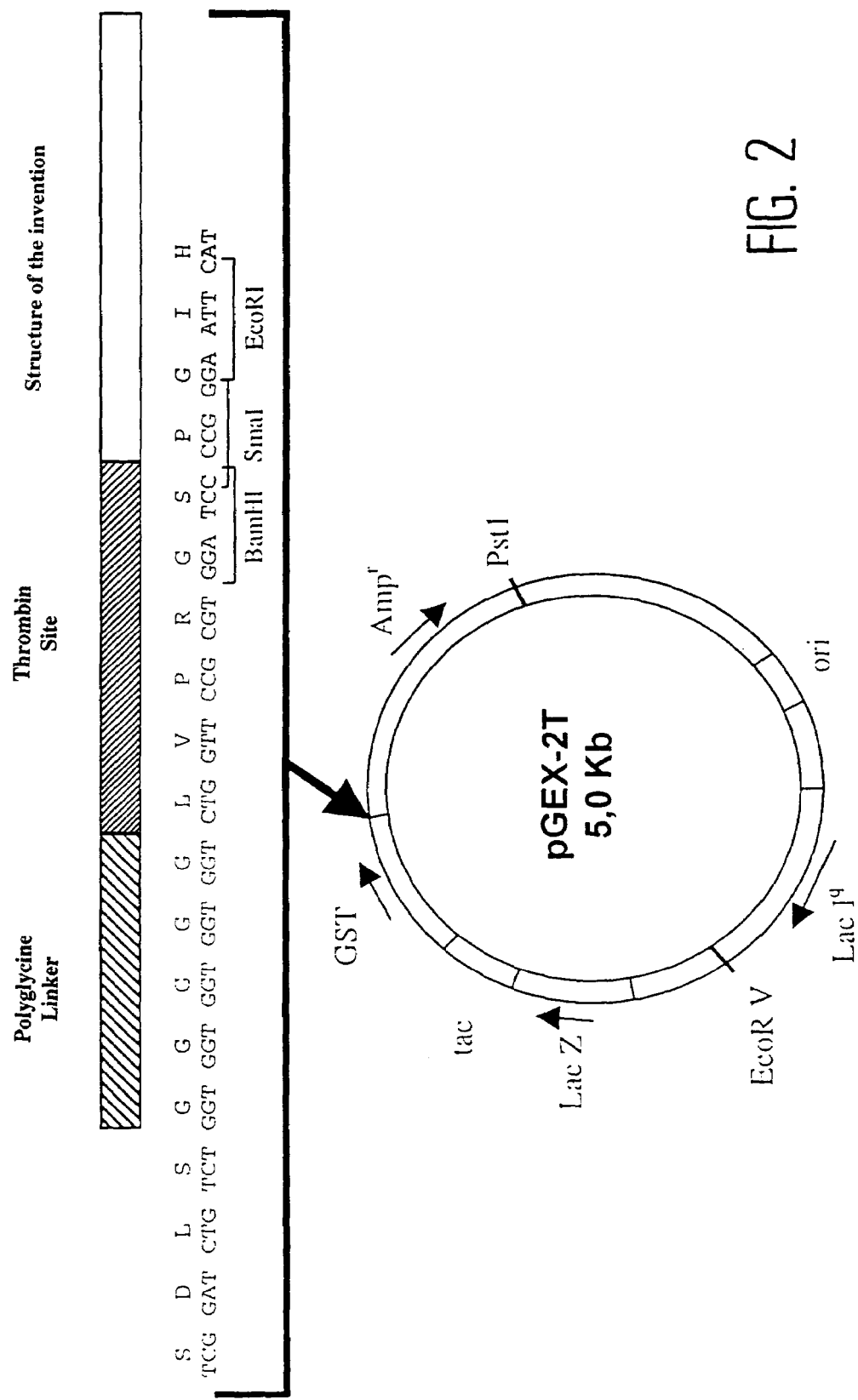
FIG. 2 is diagram illustrating the insertion of coding cDNA for the chemical structure of the present invention into a PGEX-2T vector in order to produce said compound through genetic engineering.

The cDNA of these annexins sequences was prepared by using PCR from cDNA of the corresponding annexins. The cDNA was inserted into the pGEX-2T vector (Smith & Johnson, 1998). FIG. 2 is a diagram illustrating the insertion of cDNA into the vector. Absence of mutations induced by PCR was controlled by sequencing. Production of the peptide is achieved by using the *E. Coli* BL21 strain containing the expression vector described earlier. After induction by isopropylthiogalacto-pyranoside (IPTG, 100 μm) to an optical density of 1 to 600 nm, growth was continued until a plateau was reached, i.e., for about 3 hours. After centrifugation, bacteria were resuspended in the lysis buffer comprising, 50 mM Tris-HCl, pH 8, 10 mM EDTA, 500 mM NaCl, 5% (v/v) glycerol, 1% (n/v) Triton X100, 1 mM dithiothreitol (DTT), 1 mM phenylmethylsulfonyl fluoride (PMSF) and 20 μg/ml of aprotinin.

Purification was carried out in the following way: after sonication and centrifugation at 10,000 g, the supernatant containing the soluble proteins is incubated with glutathion/agarose beads providing the bond specific to these beads, of GST domain fusion protein. After washing with a solution containing 1 M NaCl, 50 mM Tris-HCl at pH 8, 70 units of thrombine per liter of culture medium were added and the sequence is eluated.

The sequence is then purified on a proRPC (trade name) column of type 16/10, provided by Pharmacia, by using a FPLC system and a linear gradient of Millipore (trade name) grade water containing 0.1% (v/v) of trifluoracetic acid TFA, and acetonitrile containing 0.1% of TFA. The flow rate is adjusted to 2.5 ml/mn. The sequence is then freeze-dried. The final yield is about 8 mg of sequence per liter of culture medium.

Example 2

Stability of the ID No.1 Sequence of Annexin I

Various experiments show that this sequence forms a stable folding protein.

Figure 3:
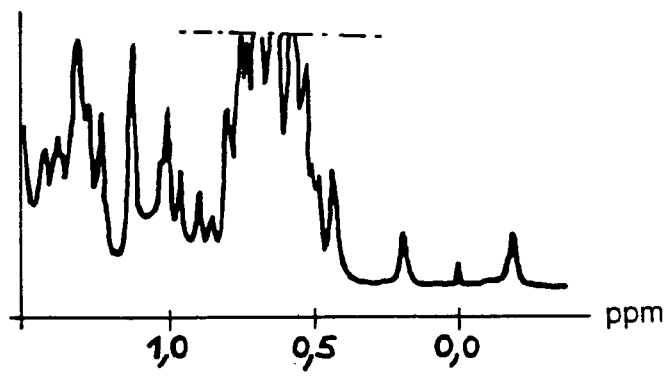
FIG. 3 is a schematic representation of a $^1$H NMR spectrum of domain 1 of the present invention of annexin I showing the aliphatic region.

FIG. 3 shows a one-dimensional $^1$H NMR spectrum of the proton of the ID No.1 sequence isolated from annexin I, in an aqueous solution. Dispersion of resonance frequencies and the presence of resonances at chemical shifts less than 0 ppm clearly show that this sequence is highly structured. Furthermore, the chemical shift data of a protons reveal the presence of 5 helices in agreement with the crystallographic structure.

Figure 4:
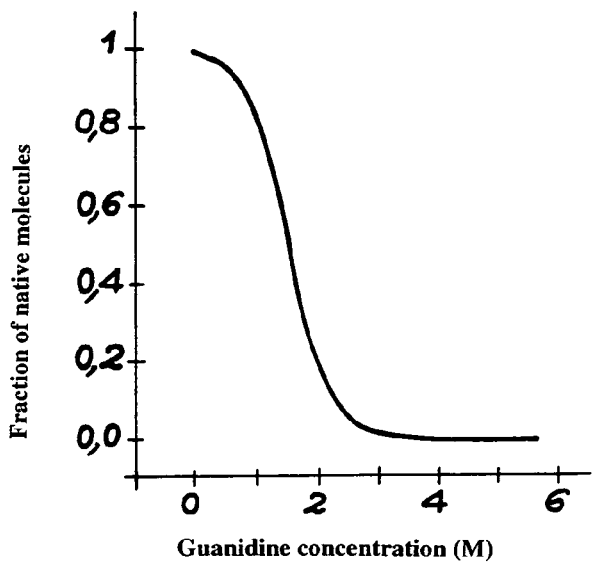
FIG. 4 is a graphical representation of denaturation of domain 1 of the present invention of annexin I with guanidinium chloride.
Figure 5:
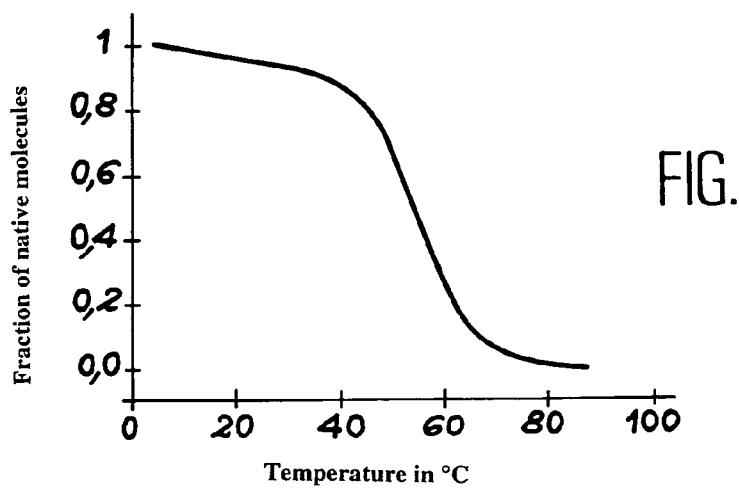
FIG. 5 is a graphical representation of thermal denaturation of domain 1 of the present invention of annexin I.

FIG. 4 shows the cooperative denaturation of domain 1 of annexin I issued from ID No.1 sequence, with guanidinium chloride, which is a standard denaturation agent and FIG. 5 shows the cooperative denaturation of the sequence with temperature.

Analogous data are obtained for the other sequences described earlier and they demonstrate that certain annexin sequences behave like small proteins of normal stability, which may be used directly or as a platform for the engineering of novel functional compounds.

Example 3-1

The Essential Role of Domain 1 of Annexin V Issued from ID No.2 Sequence in the Binding of Annexin V to the Membranes Binding experiments of annexin V to model membrane systems as well as kinase c protein (PKC) in vitro and cytoplasmic (cPLA$_2$) phospholipase A$_2$ (PLA$_2$) in vivo inhibition experiments demonstrate the essential role played by domain 1 in this bonding to membranes.

The case of CPLA$_2$ inhibition is taken here as an example. Inhibition of phospholipasic activity by annexin V results from the depletion of the lipid substrate common to both of these proteins. Various mutants of annexin V were constructed in order to selectively eliminate in one or several domains the calcium bonding capacity, i.e., the phospholipids. The mutation consists of replacing the bidentate ligand of calcium, Glu or Asp, of a sequence of the present invention with a non-binding residue, respectively Gln or Asn. Twelve mutants were thus constructed and purified: M1, M2, M3, M4, M1M2, M1M3, M1M4, M2M3, M1M2M3, M1M2M4, M2M3M4 and M1M2M3M4, the number designating the domain for which the calcium binding capacity is suppressed. All the results show that the phospholipasic activity of cell PLA$_2$, measured by the desalting rate of arachidonic acid, strongly depends on the presence of the calcium site in domain 1 and to a lesser extent in domain 4. Suppression of calcium sites in domains 2 and 3 has virtually no effect on the inhibition of phospholipasic activity of CPLA$_2$. (Mira et al. J. Biol. Chem. 1997, 272:10474–10482; Dubois et al. Biochem. J. 1998, 330: 1277–1282).

The following Table (I) groups together certain results of this example and shows the percentage of reduction in the binding capacity of mutants from annexin V to phospholipids as compared with wild annexin V.

| Wild annexin V | M1 | M2 | M3 | M4 | M1M2M3 | M1M2M4 |
|---|---|---|---|---|---|---|
| 0 | 79 ± 6 | 38 ± 4 | 47 ± 9 | 38 ± 6 | 98 ± 1 | 85 ± 7 |

This table (I) shows the binding of membranes of annexin V and of its mutants M1, M2, M3, M4, M1M2M3 and M1M2M4. Results are expressed as a percentage of the reduction in binding capacity as compared with wild annexin V (mean value±standard error). For mutants M123 and M124, the residual binding rate is insignificant.

Example 3-2

Preliminary Results Concerning the Binding of Annexin V and of Various Mutants to Model Membranes Consisting of Phosphatidylcholine and Phosphatidyl-Serine The following mutants of human annexin V were prepared according to the method described in Example 1:

M1M2M3M4: The main calcium site corresponding to the AB loop, is suppressed in all the domains by a mutation of the bidentate ligand.

M2M3M4: The main calcium site of domains 2, 3 and 4 is suppressed by a mutation of the bidentate ligand, the one of domain 1 subsists.

M2M3M4-Arg22Ala-Arg63Ser: Suppression of ligands L2 and L3 of the PS site of the present invention.

M2M3M4-Arg22Ala-Arg63Ser-Lys29AlaAsp68Ile/Phe/Trp: Suppression of all the ligands of the PS site of the present invention except that those concerning the calcium site are preserved.

The binding capacity of mutants of annexin V to PC/PS membranes is then compared with that of the wild form according to the following protocol:

A homogeneous mixture of PC/PS in a proportion of 80/20 is suspended in solutions containing variable calcium concentrations of 0, 30, 100, 1000 $\mu$M. The various proteins are then introduced and incubated for a few minutes. The suspension is then centrifuged by ultra-centrifugation at 90,000 rpm. The membranes settle at the bottom of the tube. The supernatant called S1, is entirely picked up for subsequent analysis of protein content which will provide information on the amount of protein not bound to the membrane. The membrane sediment is then dispersed in a solution containing EDTA in a sufficient amount for desalting the proteins, binding of annexin V being reversible and dependent on calcium. The suspension is again centrifuged and a second supernatant called S2, is recovered. Protein content analysis of S2 provides information concerning the amount of proteins which are fixed to the membrane.

The analysis of the supernatants is carried out by electrophoresis on polyacrylamide gel in a standard way which does not need to be described herein.

Figure 9:
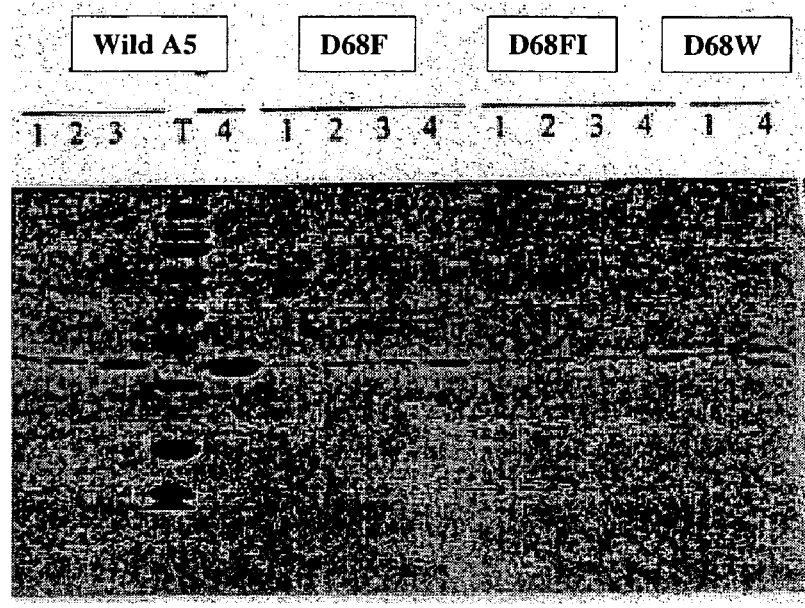
FIGS. 9A and 9B are photographs of poly-acrylamide gels which illustrate the fixing of annexin V and of certain of its mutants on membranes consisting of phosphatidylcholine and phosphatidylserine (supernatant S2).
Figure 9B:
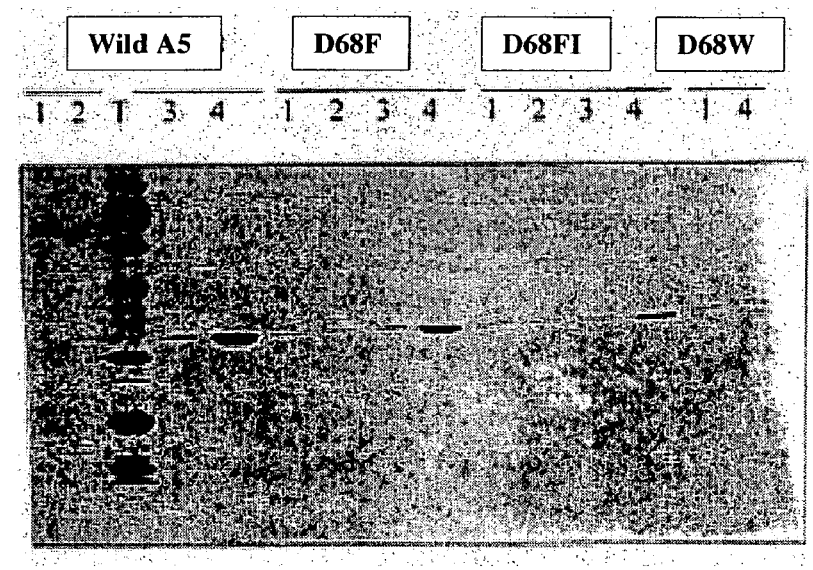

The appended FIGS. 9A and 9B show all the results.
In this figure:
Wild: A5=annexin V
Mutants:
D68F=M2M3M4-Arg22Ala-Arg63Ser-Lys29Ala-Asp68Phe
D68I=M2M3M4-Arg22Ala-Arg63Ser-Lys29Ala-Asp68Ile
D68W=M2M3M4-Arg22Ala-Arg63Ser-Lys29Ala-Asp68Trp
1, 2, 3, 4=calcium concentration 0, 30, 100, 1,000 $\mu$M, respectively
T=molecular mass standards.

Comparison of the behavior of M1M2M3M4 and M2M3M4 mutants with that of wild annexin V clearly shows that virtually the binding to the membranes in presence of calcium is exclusively provided by domain 1, i.e., which contains the claimed PS site. This result confirms those given in Example 3-1 above.

Behavior of mutants M2M3M4-Arg22Ala-Arg63Ser and M2M3M4-Arg22Ala-Arg63Ser-Lys29Ala-Asp68Ile/Phe/Trp shows that the binding to the membranes is considerably attenuated when ligands L2, L3, L4 and L5 are suppressed. However the bond is not totally suppressed to the extent that the LCa5, Ca ligands which are part of the calcium site subsist and still provide a binding of PS but with a very reduced affinity;

Example 4

Use of the Chemical Structure of the Present Invention

Three utilization schemes are provided: i) simple engineering of the domains in order to meet various requirements related to their use as research, diagnose and therapeutic tools; ii) redesign of the platform which forms the topology of the domain into a new simpler platform which may be synthetized chemically or through genetic engineering; iii) replacement of the peptide or peptoid platform with a non-peptide organic structure for producing a drug. in the three cases, the purpose is naturally to preserve, or even improve, spatial localization of phospholipid binding functions, as described earlier.

1) Annexin Domain Engineering

The annexin domains of the present invention form peptide platforms. Modification of the domain's sequence through mutagenesis is understood under the term of engineering, in order to improve the general stability of the molecule and to adapt it to the physico-chemical conditions imposed by its use, to improve its affinity for the phospholipid ligand and to provide it with a specificity, specific to each phospholipid. The aim is also to allow for introduction of various tracers for different applications which are discussed later. Our present knowledge is largely sufficient for carrying out such engineering.

Examples of a change in properties are illustrated in Example 4. They were obtained through a standard genetic engineering technique with mutation of the involved amino acids.

2) Redesign of Peptide Platforms

Redesign of the platform consists in redefining a molecular architecture, while maintaining the appropriate topology of the residues involved in the binding to calcium or to phospholipids. The redesign is important for generating a shorter sequence platform which may be produced by chemical synthesis. The synthesis of a peptide of the size of a domain is feasible but remains difficult. However, by reducing the number of residues by half, i.e., about 35 residues, it is currently possible to carry out the synthesis. In this redesign operation, geometry is rather precisely preserved, allowing for interactions with phospholipid and notably for positioning of residues of the annexin sequence. These residues are those shown in bold in FIGS. 6a–6d for annexins (I) to (V).

Figure 7:
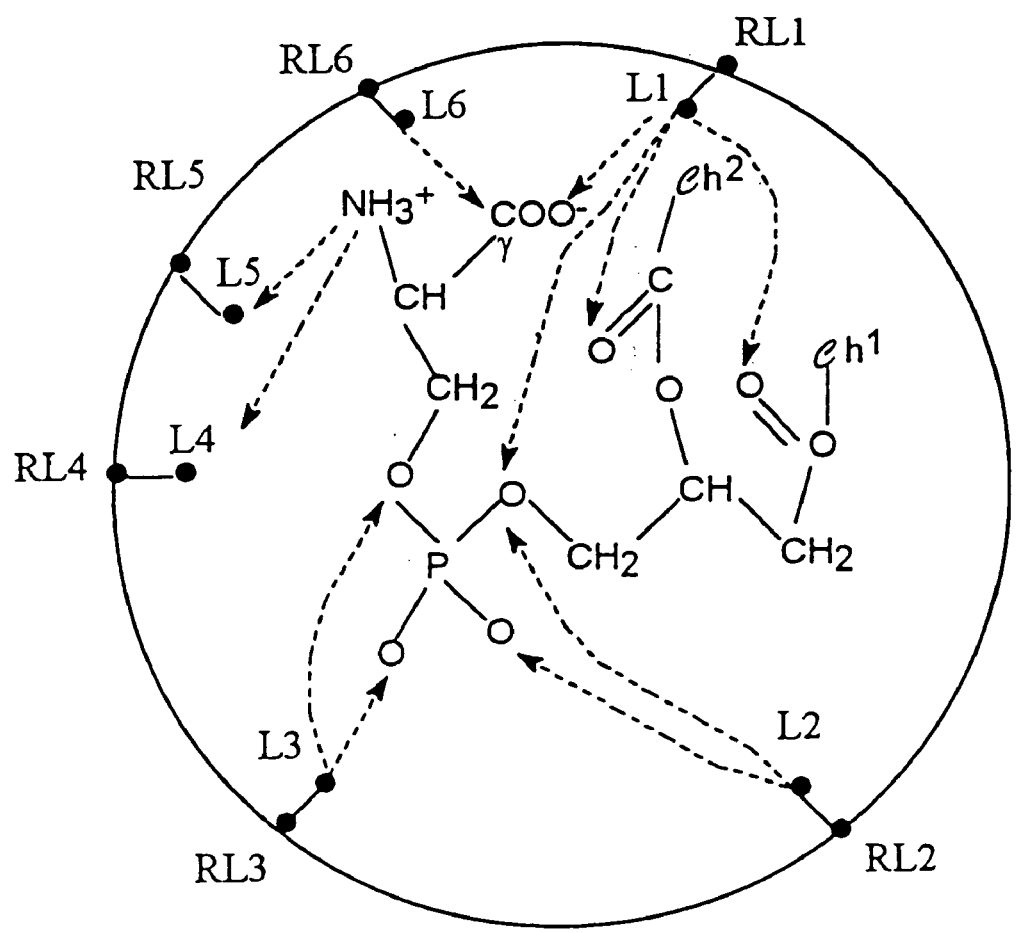
FIG. 7 is a schematic representation of the structure of construction (I) of the present invention bound to a phosphatidylserine molecule demonstrating the interactions between the binding functions L1 to L6 of the structure of construction (I) of the invention and a phosphatidylserine molecule.
Figure 8:
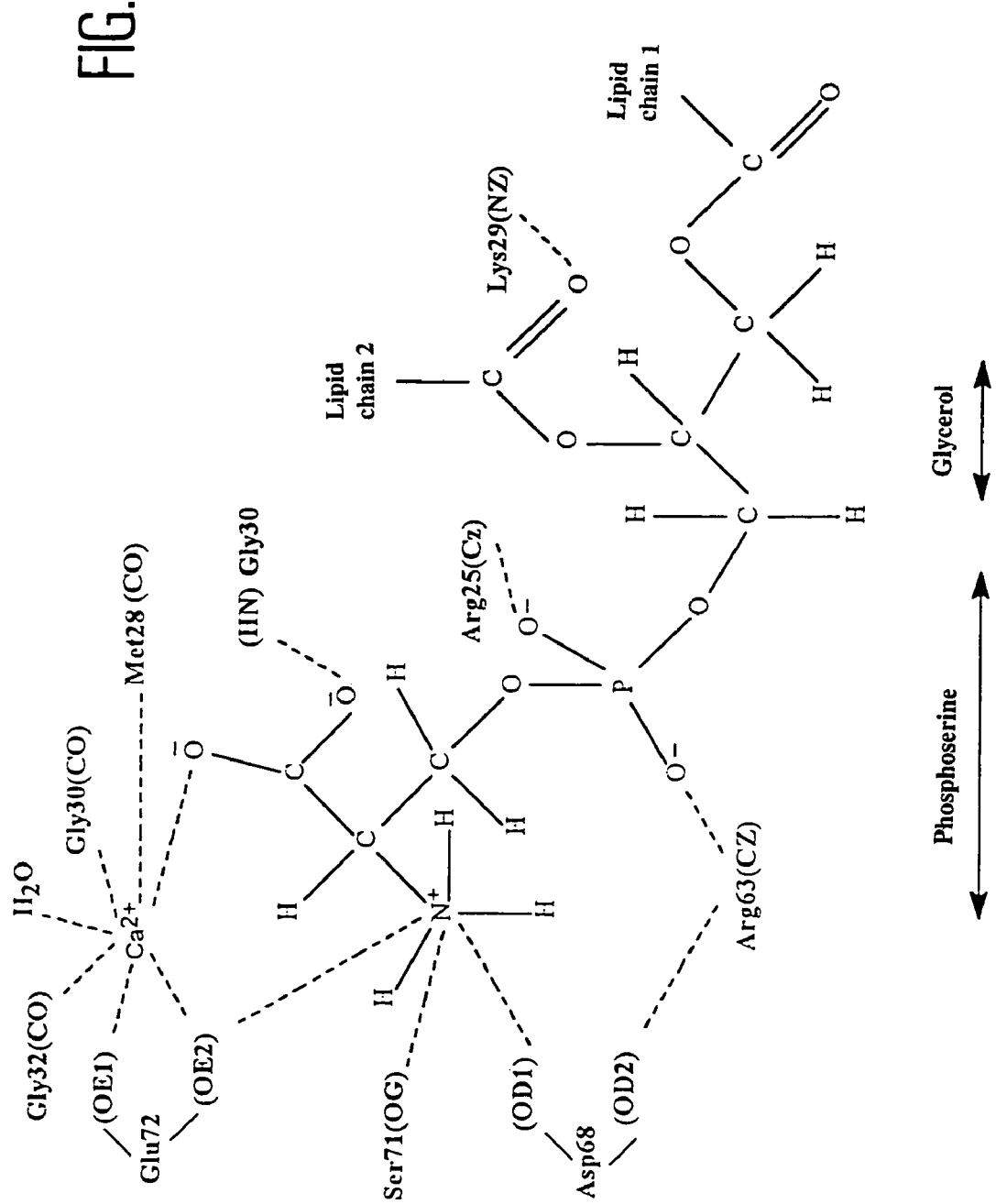
FIG. 8 is a schematic representation of interactions between the residual ligands of domain 1 of the present invention of human annexin V illustrated in FIG. 6*b*, and a phosphatidylserine molecule in the presence of a calcium atom.

This set comprises two basic residues generally Arg-x-x-x-Lys, at the end of the A helix of the relevant domain and a series of acid, basic and neutral residues, generally Arg-x-x-x-x-Asp-x-x-Ser-Asp, located in the D helix. Study of the molecular structure as in FIGS. 7 and 8, shows that these residues are perfectly positioned for binding a phosphatidylserine molecule. The carboxylate group of this lipid is itself bound to the calcium atom in the AB loop and designated in the following as the "AB calcium site".

The sequence:

Arg-xxx-Lys(helix A)----Arg-x-x-x-x-Asp-x-x-Ser-Asp(helix D)

associated with that of the AB calcium site, is therefore a consensus sequence for the binding of phosphatidylserine in the compounds of the present invention. As a generalization, this sequence will now be designated as:

RL1-x-x-x-RL2----RL3-x-x-x-x-RL4-x-x-RL5-RL6 wherein RL1–RL6 are the essential residual ligands in the phosphatidylserine bond shown in bold in the sequences of FIGS. 6a–6d and indicated in the structure compounds (I)–(VI). The consensus sequence of the AB calcium site is the succession:

Met-Lys-Gly-x-Gly-Thr----Asp(or Glu)

The calcium ligands are the peptide carboxyl groups of the residues in italics (residues of the AB loop) in the figure and both oxygen atoms of the carboxylate group of the side chain of residue Asp (or Glu) at the end of the D helix, also named as the bidentate ligand. As a generalization, these calcium ligands will now be designated as:

RCa1-RL2-RCa2-x-RCa3-Thr----(RCa4RCa5) or RL6

In the case of annexin, RCa4 and RCa5 form a single and same residue already identified earlier as RL6.

The interatomic distance data between the residual ligands are given in the following Table (II) with reference to appended FIG. 7 and the specific domain-calcium-phosphatidylserine interactions are indicated in the following Table (III) with reference to the appended FIG. 8.

In FIG. 8, Ch1 and Ch2 represent the location of possible carbon chains of the phospholipid. These chains may be the ones described, for example arachidonic acid.

According to the invention, the chemical structure may be formed in the following way:

a) it includes in particular at least 6 residues, so-called residual ligands, named RL 1–RL6 and their nature is the following:

RL1=Arg or Lys or Orn
RL2=Arg or Lys or Orn
RL3=Arg or Lys or Orn
RL4=Asp or Glu
RL5=Ser or Thr or Asp or Glu
RL6=Asp or Glu b) The α carbon atoms of residual ligands RL1–RL6 are positioned in space so that the side chains are directly accessible to the phospholipids.

c) The α carbon atoms of residual ligands RL1–RL6 are positioned according to the following table of distances (II):

| 60 carbon atom | RL2 | RL3 | RL4 | RL5 | RL6 |
|---|---|---|---|---|---|
| RL1 | 0.45–0.65 | 0.7–1.2 | 0.7–1.0 | 0.85–1.15 | 0.65–0.95 |
| RL2 | | 0.5–1.05 | 0.8–1.2 | 1.2–1.7 | 0.9–1.4 |
| RL3 | | | 0.5–1.08 | 1.0–1.3 | 1.2–1.7 |
| RL4 | | | | 0.45–0.75 | 0.7–1.2 |
| RL5 | | | | | 0.4–1.2 | d) The side chains of residual ligands RL1–RL6 may establish a network of hydrogen bonds with phosphatidylserine according to the diagram where the arrows → designate at least a hydrogen bond, in FIG. 8, in the direction from donor to acceptor and L1–L 6 designate the ligands of phosphatidylserine according to the following list:

L1=NZLys or CZArg of RL1
L2=NZLys or CZArg of RL2
L3=NZLys or CZArg of RL3
L4=CGAsp or CDGlu of RL4
L5=CB of Ser or Thr or CG of Asp or CD of Glu of LR5
L6=NZLys or CZArg of RL6
HN=H
NZ=N zeta
CZ=C zeta
OD=O delta
OG=O gamma
OE=O epsilon wherein distances between ligands L1–L6 and phosphatidylserine atoms are given in the following table (III):

Distances nm×10

|    | N | Cβ | Cγ | O1 | O2 | O3 | O4 | C1 Chain Ch1 | C1 Chain Ch2 |
|---|---|---|---|---|---|---|---|---|---|
| L1 | 0.35–0.65 | 0.3–0.5 | 0.25–0.45 | 0.2–0.35 | 0.25–0.5 | 0.35–0.6 | 0.2–0.35 | 0.4–0.7 | 0.5–0.8 |
| L2 | 0.55–0.85 | 0.45–0.75 | 0.45–0.75 | 0.4–0.6 | 0.2–0.4 | 0.4–0.6 | 0.25–0.45 | 0.7–1.1 | 0.7–1.1 |
| L3 | 0.4–0.6 | 0.4–0.6 | 0.45–0.75 | 0.4–0.6 | 0.2–0.4 | 0.2–0.35 | 0.25–0.5 | 0.7–1.1 | 0.6–1.0 |
| L4 | 0.25–0.45 | 0.3–0.5 | 0.35–0.55 | 0.55–0.85 | 0.5–0.75 | 0.4–0.65 | 0.4–0.6 | 0.8–1.2 | 0.8–1.2 |
| L5 | 0.25–0.5 | 0.45–0.65 | 0.5–0.75 | 0.65–0.95 | 0.65–0.95 | 0.5–0.8 | 0.5–0.9 | 0.8–1.2 | 0.6–1.0 |
| L6 | 0.3–0.5 | 0.35–0.55 | 0.3–0.45 | 0.65–0.95 | 0.7–1.0 | 0.65–0.95 | 0.5–0.8 | 0.6–1.0 | 0.8–1.2 |

For ligand L1, at least two of the five distances shown in this table are preferably complied with.

3) Organic Platform

The third step is the final step for obtaining a drug which is easily used orally. It consists in replacing the peptide platform with an organic structure in compliance with the spatial positioning of the phospholipid ligands. The calcium and phospholipid ligands are no longer amino acid residues but chemical functions reproducing the interactions described earlier.

With the organic structures currently used in pharmacology, it is possible to build stiff platforms capable of having a site for binding the phospholipid, according to the invention. These structures may be formed through conventional chemical techniques known to one skilled in the art, for which a reminder is unnecessary here.

Example 5

Very advantageously, use of a structure or assembly of the present invention may be made as indicated earlier in three directions: research, diagnose and therapeutics.

1) Research

For these experiments, it is appropriate to couple a structure of the present invention with a labelling molecule enabling a detection to be performed. These labelling molecules may be the aforementioned ones, for example the fluorescent molecules, an avidin-biotin system, radioelements and generally speaking, those currently used.

2) Diagnose

The chemical structures and assemblies of the present invention may be used, as indicated earlier, for "in vitro" detection of pathologies involving the occurrence of negative charges at the surface of cells and the release of microvesicles in blood: for example, coagulation disorders, acute inflammatory pathologies, etc.

They may also be coupled with short-lived radioelements and with "in vivo", detection of the localization of thrombotic areas during vascular accidents of any kind, in particular cerebrovascular accidents, through the use of imaging systems.

They may also be coupled with paramagnetic compounds, for example a gadolinium complex, and with "in vivo" detection of the localization of thrombotic areas during vascular accidents of any kind, in particular cerebrovascular accidents, by using magnetic resonance imaging (MRI).

The aforementioned couplings may be achieved through standard organic chemistry techniques known to one skilled in the art, for which a reminder is unnecessary here.

3) The Drug

The structures and assemblies of the present invention may be used as such for producing a drug which may be used for a treatment or a prophylaxis since they have intrinsic anticoagulant, antithrombolytic and anti-inflammatory properties.

With the assemblies according to the invention, a cladding of cell surfaces may be achieved, capable of blocking access of compounds involved in the primary stages of blood coagulation and inflammatory phenomena at these surfaces.

The structures and assemblies of the present invention may also be used for targeting molecules at a site of the thrombus, of the inflammation, or towards a tumor area.

In this use, the structures and assemblies of the present invention are coupled with a molecule which has a thrombolytic action, with a molecule which has an anti-inflammatory action or with a molecule which has an anti-tumor action, respectively.

The structures and assemblies of the present invention may therefore for example be used for producing a drug which may be used in the treatment and prophylaxis of thrombosis. Coupling of these structures and assemblies to molecules with thrombolytic action allows the latter to be targeted towards the thrombogenic areas. Thrombolytic molecules such as streptokinase, urokinase and plasminogen activators may be used.

Structures and assemblies of the present invention may also be used coupled with a molecule having an anti-inflammatory action in order to produce a drug which may for example be used locally or orally in acute pathologies like asthma, HRC, Crohn's decease, septic shock, collagenosis and arthritis.

The structures and assemblies of the present invention may also be used coupled with a molecule having an anti-tumor action. This coupling enables the latter molecule to be targeted towards the areas bearing negative charges such as tumors having apoptotic cell centers, inflammatory tumors, etc.

The structures and assemblies of the present invention may also be used for producing a cover material for biomaterials likely to be thrombogenic. A thrombogenic biomaterial covered in this way loses its thrombogenic properties. For example, the thrombogenic biomaterial may be a heart valve.

The invention provides the use of a chemical structure derived from proteins of the annexin family and their isolated, changed or unchanged domains, capable of binding reversibly to lipid effectors such as phosphatidylserines, phosphatidic acids, phospha-tidylethanolamines and phosphatidylinosito-phosphates. The aim is to provide a set of protein, peptide, peptoid and organic compounds, for which the main property is specific recognition of the occurrence of lipid signals at the surface of cell membranes in relationship with the normal or pathological functioning of tissues. Pathologies especially targeted by the invention are: (i) blood coagulation disorders, (ii) apoptosis phenomena subsequent to the action of chemical compounds, physical effects like ionizing radiation, biological effects like those related to the formation or necrosis of cancerous tissues, in addition to the normal phenomena of apoptosis, (iii) acute inflammatory pathologies and (iv) disorders associated with relationships between the cells and the extra-cellular matrix and notably with collagen.

In addition to the complete engineering of entire annexins, one of the aspects of the invention is the use of annexin covalent modules and domains either directly or as a platform for the engineering of functional peptide compounds. The aim is to use these domains and modules either in their natural form, or modified through mutagenetic or chemical routes, to transform them into compounds meeting the biological criteria discussed in the previous paragraph.

Because of their small size, these domains may easily be associated with other proteins either for forming multifunctional chimera proteins, or for introducing a controlling mechanism by effectors other than the signalling phospholipid. Further, the invention provides redefinition, through protein engineering methods, of the specificity of domains for the different signalling lipids mentioned above.

The invention finally provides reconstruction of these domains, through a novel design, in order to transform them into compounds with a more limited size and accessible to peptide synthesis and in particular to the introduction of non-natural amino acid residues with the purpose of increasing the lifetime of these compounds in the organism.

What is claimed is:

1. An isolated polypeptide, consisting of a sequence with the following formula:

$$X\text{-}RL1\text{-}N^1\text{-}RL2\text{-}M\text{-}RL3\text{-}N^2\text{-}RL4\text{-}N^3\text{-}RL5\text{-}RL6\text{-}Y$$

wherein $N^1$ to $N^3$ each independently represent 1 to 4, independently selected, natural or non-natural, amino acids and wherein M is a peptide consisting of 1 to 100 natural or non-natural amino acids;

wherein RL1, RL2, and RL3 are independently selected from Lys, Arg or Orn; RL4 and RL6 are independently selected from Asp or Glu; and RL5 is independently selected from Ser, Thr, Asp, or Glu; and wherein X is a sequence of 9–11 amino acids and Y is a sequence of 14–19 amino acids.

2. The isolated polypeptide according to claim 1, wherein $N^1$ represents three amino acids, $N^2$ represents four amino acids, and $N^3$ represents two amino acids.

3. The isolated polypeptide according to claim 1, wherein M is a peptide consisting of 33 natural or non-natural amino acids.

4. The isolated polypeptide according to claim 1, wherein the structure of formula (VII) is a polypeptide sequence selected from the peptide sequence from Arg124 to Asp171 of SEQ ID NO: 1, the peptide sequence from Arg25 to Glu72 of SEQ ID NO: 2, the peptide sequence from Lys100 to Glu147 of SEQ ID NO: 3, the sequence from Arg24 to Glu71 of SEQ ID NO: 4, the sequence from Arg97 to Asp144 of SEQ ID NO: 5 or a modified sequence of these sequences provided that RL1, RL2, and RL3 are independently selected from Lys, Arg or Orn; RL4 and RL6 are independently selected from Asp or Glu; and RL5 is independently selected from Ser, Thr, Asp, or Glu.

5. The isolated polypeptide according to claim 1, further comprising a calcium site where the calcium ion is complexed by this site forms one of the ligands of the negatively charged phospholipid.

6. The polypeptide according to claim 1, wherein said polypeptide has an affinity for a phospholipid selected from a phosphatidylserine, a phosphatidylethanolamine, a phosphatidylinositol, a phosphatidic acid, and a cardiolipin.

7. A method for producing a polypeptide as defined in claim 1, comprising preparing a cDNA comprising a coding sequence of bases for said polypeptide, inserting the cDNA in an appropriate expression vector, and transforming an appropriate host cell producing said polypeptide by translation of said cDNA.

8. The method according to claim 7, wherein the vector is a plasmid.

9. The method according to claim 7, wherein the vector is a pGEX-2T vector.

10. The method according to claim 7, wherein the appropriate host cell is E. Coli.

11. A pharmaceutical composition comprising a polypeptide as defined in claim 1 and an inert material.

12. A method of treating a thrombosis, tumor or inflammation with the pharmaceutical composition claimed in claim 11.

13. A method for producing a material for covering thrombogenic biomaterial comprising incorporating a polypeptide as claimed in claim 1.

14. A labelling compound comprising a polypeptide as defined in claim 1 coupled with a labelling molecule.

15. The compound according to claim 14, wherein the labelling molecule is selected from a fluorescent molecule, the avidin-biotin complex, a radioelement, and a paramagnetic compound.

16. A diagnostic kit comprising a compound according to claim 14.

17. The diagnostic kit according to claim 16, further comprising an adequate reagent enabling said labelling molecule to be detected.

18. A kit for analyzing and detecting negative charges at the surface of cells, comprising a polypeptide according to claim 1, coupled with a tracer.

19. A kit for analyzing and detecting microvesicles in blood at the surface of cells, comprising a polypeptide according to claim 1, coupled with a tracer.

20. The isolated polypeptide according to claim 1, wherein

X is selected from the group consisting of TPAQFDADEL (residues 114–123 of SEQ ID NO: 1), DERADAETL (residues 16–24 of SEQ ID NO: 2), PPAVFDAKQL (residues 90–99 of SEQ ID NO: 3), NAMEDAQTL (residues 15–23 of SEQ ID NO: 4), and PTVLYDVQELQ (residues 1–11 of SEQ ID NO: 5); and Y is selected from the group consisting of TSGDFRNALLSLAKG (residues 172–186 of SEQ ID NO: 1), LTGKFEKLIVALMKPSRLY (residues 73–91 of SEQ ID NO: 2), TSGDFRKALLTLADG (residues 148–162 of SEQ ID NO: 3), LSGNFEQVIVGMMT (residues 72–85 of SEQ ID NO: 4), and TSFMFQRVLVSLSAGG (residues 145–160 of SEQ ID NO: 5).

21. The isolated polypeptide according to claim 1, wherein X is the polypeptide sequence TPAQFDADEL (residues 114–123 of SEQ ID NO: 1) and Y is the polypeptide sequence TSGDFRNALLSLAKG (residues 172–186 of SEQ ID NO: 1).

22. The isolated polypeptide according to claim 1, wherein X is the polypeptide sequence DERADAETL (residues 16–24 of SEQ ID NO: 2) and Y is the polypeptide sequence LTGKFEKLIVALMKPSRLY (residues 73–91 of SEQ ID NO: 2).

23. The isolated polypeptide according to claim 1, wherein X is the polypeptide sequence PPAVFDAKQL (residues 90–99 of SEQ ID NO: 3) and Y is the polypeptide sequence TSGDFRKALLTLADG (residues 148–162 of SEQ ID NO: 3).

24. The isolated polypeptide according to claim 1, wherein X is the polypeptide sequence NAMEDAQTL (residues 15–23 of SEQ ID NO: 4) and Y is the polypeptide sequence LSGNFEQVIVGMMT (residues 72–85 of SEQ ID NO: 4).

25. The isolated polypeptide according to claim 1, wherein X is the polypeptide sequence PTVLYDVQELQ (residues 1–11 of SEQ ID NO: 5) and Y is the polypeptide sequence TSFMFQRVLVSLSAGG (residues 145–160 of SEQ ID NO: 5).

26. An isolated polypeptide, consisting of a sequence with the following formula:

$$X\text{-}RL1\text{-}N^1\text{-}RL2\text{-}M\text{-}RL3\text{-}N^2\text{-}RL4\text{-}N^3\text{-}RL5\text{-}RL6\text{-}Y$$

wherein $N^1$ to $N^3$ each independently represent 1 to 4, independently selected, natural or non-natural, amino acids and wherein M is a peptide consisting of 1 to 100 natural or non-natural amino acids;

wherein RL1, RL2, and RL3 are independently selected from Lys, Arg or Orn; RL4 and RL6 are independently selected from Asp or Glu; and RL5 is independently selected from Ser, Thr, Asp, or Glu; and wherein X is the polypeptide sequence TDFPGFDERADAETL (residues 10–24 of SEQ ID NO: 2) and Y is the polypeptide sequence LTGKFEKLIVALMKPSRLY (residues 73–91 of SEQ ID NO: 2).

27. An isolated polypeptide, consisting of a sequence with the following formula:

$$X\text{-}RL1\text{-}N^1\text{-}RL2\text{-}M\text{-}RL3\text{-}N^2\text{-}RL4\text{-}N^3\text{-}RL5\text{-}RL6\text{-}Y$$

wherein $N^1$ to $N^3$ each independently represent 1 to 4, independently selected, natural or non-natural, amino acids and wherein M is a peptide consisting of 1 to 100 natural or non-natural amino acids;

wherein RL 1, RL2, and RL3 are independently selected from Lys, Arg or Orn; RL4 and RL6 are independently selected from Asp or Glu; and RL5 is independently selected from Ser, Thr, Asp, or Glu; and wherein X is the polypeptide sequence KAASEFNAMEDAQTL (residues 9–23 of SEQ ID NO: 4) and Y is the polypeptide sequence LSGNFEQVIVGMMT (residues 72–85 of SEQ ID NO: 4).

* * * * *